(12) United States Patent  
Ammar

(10) Patent No.: US 10,213,091 B2  
(45) Date of Patent: Feb. 26, 2019

(54) SYSTEM, METHOD, AND APPARATUS FOR VISUALIZING AND IDENTIFYING PATHOLOGICAL TISSUE

(71) Applicant: University of Dammam, Dammam (SA)

(72) Inventor: Ahmed Sabry Ammar, Dammam (SA)

(73) Assignee: University of Dammam, Dammam (SA)

( * ) Notice: Subject to any disclaimer, the term of this patent is extended or adjusted under 35 U.S.C. 154(b) by 875 days.

(21) Appl. No.: 14/621,483

(22) Filed: Feb. 13, 2015

(65) Prior Publication Data

US 2016/0235275 A1    Aug. 18, 2016

(51) Int. Cl.
*A61B 1/04* (2006.01)
*A61B 1/00* (2006.01)

(52) U.S. Cl.
CPC ...... *A61B 1/00009* (2013.01); *A61B 1/00085* (2013.01); *A61B 1/00154* (2013.01); *A61B 1/043* (2013.01)

(58) Field of Classification Search
CPC . A61B 1/00085; A61B 1/00154; A61B 1/043; A61B 1/00147; A61M 25/0029; A61M 25/0668; A61M 2025/0034
USPC .......................................... 600/104, 114, 118
See application file for complete search history.

(56) References Cited

U.S. PATENT DOCUMENTS

| | | | | |
|---|---|---|---|---|
| 3,677,243 A | * | 7/1972 | Nerz | A61M 25/0668 604/161 |
| 3,682,166 A | * | 8/1972 | Jacobs | A61M 16/00 128/205.12 |
| 3,788,326 A | * | 1/1974 | Jacobs | A61M 16/00 128/207.15 |
| 4,166,469 A | * | 9/1979 | Littleford | A61M 25/007 604/164.05 |
| 4,402,685 A | * | 9/1983 | Buhler | A61L 29/049 525/931 |
| 4,411,654 A | * | 10/1983 | Boarini | A61M 25/0668 604/161 |
| 4,412,832 A | * | 11/1983 | Kling | A61M 25/0668 604/161 |

(Continued)

FOREIGN PATENT DOCUMENTS

JP    5308741 B2    10/2013

*Primary Examiner* — Timothy J Neal
*Assistant Examiner* — Jae Woo
(74) *Attorney, Agent, or Firm* — Oblon, McClelland, Maier & Neustadt, L.L.P.

(57) ABSTRACT

A histopathology system includes an elongated, cylindrical probe having scanners connected to a distal end of the probe and configured to capture digital images of tissue, a mesh net connected to the distal end of the probe and configured to grasp tissue, and control circuitry configured to expand and contract the mesh net to grasp the tissue being examined. The system includes an outer sheath into which the probe is inserted having one or more tabs extending from the outer sheath to affix the outer sheath at one or more locations. An elongated, cylindrical introducer device guides the outer sheath through a bodily orifice or surgical incision when the introducer device is inserted into the outer sheath. At least one server with processing circuitry is configured to digitally stain a tissue image obtained by the scanners of the tissue, and match the tissue images to stored tissue samples.

19 Claims, 7 Drawing Sheets

(56) References Cited

U.S. PATENT DOCUMENTS

| | | | |
|---|---|---|---|
| 4,498,902 A * | 2/1985 | Ash | A61M 25/0668 600/585 |
| RE31,855 E * | 3/1985 | Osborne | A61M 25/0668 604/161 |
| 4,512,351 A * | 4/1985 | Pohndorf | A61N 1/0551 607/117 |
| 4,581,025 A * | 4/1986 | Timmermans | A61M 25/0668 604/160 |
| 4,596,559 A * | 6/1986 | Fleischhacker | A61M 25/0668 604/161 |
| 4,888,000 A * | 12/1989 | McQuilkin | A61M 25/0668 604/160 |
| 4,983,168 A * | 1/1991 | Moorehead | A61M 25/0668 604/161 |
| 8,142,422 B2 * | 3/2012 | Makower | A61B 17/24 600/178 |
| 8,267,869 B2 | 9/2012 | Lacombe et al. | |
| 8,840,566 B2 | 9/2014 | Seibel et al. | |
| 9,186,175 B2 * | 11/2015 | Mark | A61B 1/0607 |
| 2007/0203427 A1 * | 8/2007 | Vetter | A61B 10/0041 600/564 |
| 2007/0293720 A1 | 12/2007 | Bayer | |
| 2008/0058604 A1 * | 3/2008 | Sorensen | A61B 1/32 600/208 |
| 2008/0058605 A1 * | 3/2008 | Sorensen | A61B 1/32 600/208 |
| 2009/0149716 A1 * | 6/2009 | Diao | A61B 1/00085 600/202 |
| 2010/0137846 A1 * | 6/2010 | Desai | A61B 17/221 606/2.5 |
| 2011/0137178 A1 * | 6/2011 | Tearney | A61B 5/0068 600/476 |
| 2012/0082362 A1 * | 4/2012 | Diem | A61B 5/0071 382/133 |
| 2012/0083678 A1 * | 4/2012 | Drauch | A61B 5/0075 600/310 |
| 2014/0276108 A1 * | 9/2014 | Vertikov | A61B 5/0084 600/478 |
| 2014/0323811 A1 | 10/2014 | DeSantis et al. | |
| 2014/0357956 A1 | 12/2014 | Salahieh et al. | |
| 2015/0080764 A1 * | 3/2015 | Poe | A61B 1/00135 600/586 |
| 2015/0148597 A1 * | 5/2015 | Ciulla | A61B 17/22031 600/104 |
| 2016/0174848 A1 * | 6/2016 | Ammar | A61B 5/0084 600/477 |

* cited by examiner

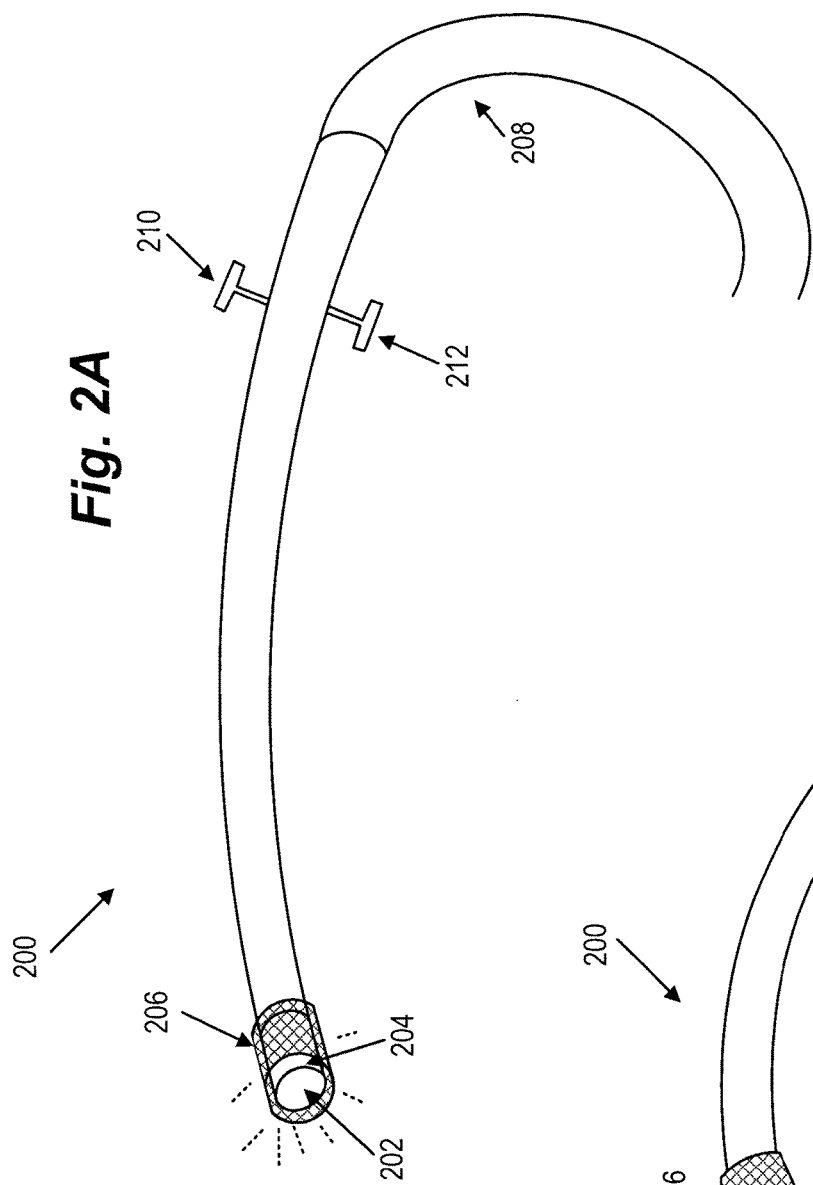
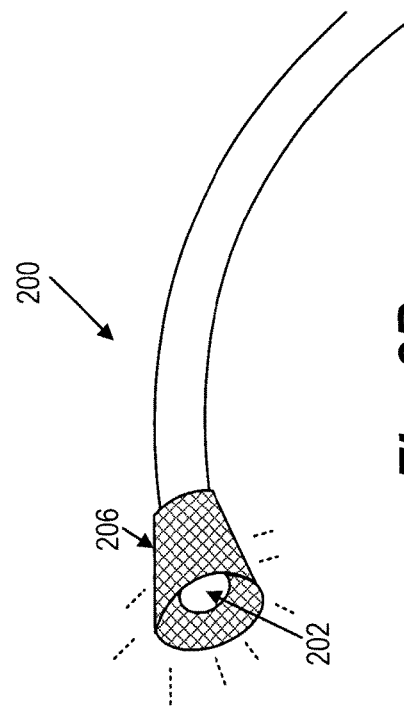

Patient: John Smith
ID#: 6645987
Date: 06/15/2013
Surgeon: Dr. J. Cook
Type of procedure: Cerebral Tissue Diagnosis Digital stain: IHC
Tissue match: Primary Glioblastoma
Location: Right parietal lobe
Magnification: 40X10
Tumor size: 3 cm
Notes: widespread cell necrosis and calcium deposits at tumor site Matched tissue image

*FIG. 6*

SYSTEM, METHOD, AND APPARATUS FOR VISUALIZING AND IDENTIFYING PATHOLOGICAL TISSUE

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

One of the challenges of removing diseased tissue from the body during surgery is that it can be difficult to distinguish healthy tissue from diseased tissue while in an intraoperative environment. Intraoperative frozen section procedures are often used to identify tissue.

SUMMARY

In an exemplary embodiment, a histopathology system includes an elongated, cylindrical probe having scanners connected to a distal end of the probe and configured to capture digital images of tissue, a mesh net connected to the distal end of the probe and configured to grasp tissue, and control circuitry configured to expand and contract the mesh net to grasp the tissue being examined. The system includes an outer sheath into which the probe is inserted having one or more tabs extending from the outer sheath to affix the outer sheath at one or more locations. An elongated, cylindrical introducer device guides the outer sheath through a bodily orifice or surgical incision when the introducer device is inserted into the outer sheath. At least one server with processing circuitry is configured to digitally stain a tissue image obtained by the scanners of the tissue and match the tissue images to stored tissue samples.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 2A is an exemplary illustration of a tissue examination probe, according to certain embodiments;

FIG. 2B is an exemplary illustration of an expanded grasping mesh on a tissue examination probe, according to certain embodiments;

FIG. 6 is an exemplary illustration of a matched tissue image with amplifying information, according to certain embodiments.

DETAILED DESCRIPTION

Figure 1A:
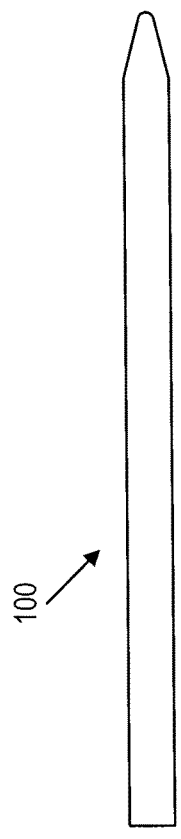
FIG. 1A is an exemplary illustration of an introducer device, according to certain embodiments.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Aspects of this disclosure are directed to a system and apparatus for visualizing and identifying pathological tissue in real time. For example, while performing neurological surgery to determine if cerebral tissue includes one or more diseased or cancerous cells, a surgeon uses a probe to obtain an image of the tissue with one or more scanners, lenses, cameras, and the like, that are attached to the probe. In certain embodiments, the probe is connected to a backend system that receives the images obtained by the probe, digitally stains the tissue images, and matches the digitally stained image to one or more images in a histopathological library. In some aspects, digital staining includes digitally enhancing or modifying the images obtained by the probe to highlight features of the images, such as cell boundaries and cell components, and may assist in distinguishing between healthy and diseased tissue.

The histopathology system allows the surgeon to diagnose the tissue as healthy or diseased in real time so that the boundaries of the diseased tissue can be determined and, if necessary, the diseased tissue can be removed without having to send tissue samples to a lab to be analyzed. The histopathology system can be implemented in neurosurgery for distinguishing healthy cerebral tissue from pathological cerebral tissue. The histopathology system can also be implemented in other medical disciplines where diagnosing cells as healthy or diseased in real time may improve an outcome for a patient, such as spinal surgery, renal surgery, gynecological surgery, hepatic surgery, general surgery, and the like. The histopathology system can also be used in non-real time environments, such as during tissue examination in a pathology lab.

Figure 1B:
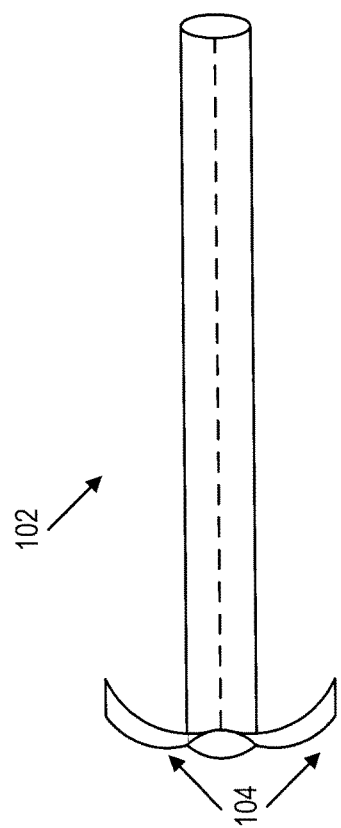
FIG. 1B is an exemplary illustration of an outer sheath, according to certain embodiments.
Figure 1C:
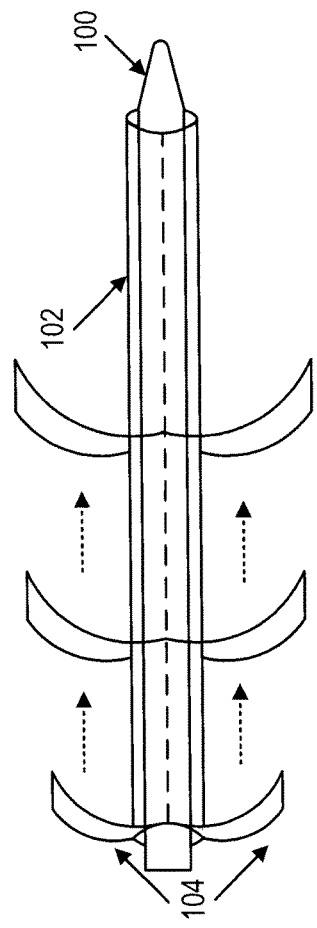
FIG. 1C is an exemplary illustration of an outer sheath surrounding an introducer device, according to certain embodiments.

FIGS. 1A-1C are exemplary illustrations of an introducer device 100 and an outer sheath 102, according to certain embodiments. The introducer device 100 is inserted into the outer sheath 102 and acts as a guide for placing the outer sheath 102 at a desired location during a tissue examination procedure.

FIG. 1A is an exemplary illustration of the introducer device 100, according to certain embodiments. The introducer device 100 is an elongated, cylindrical member made of a strong, lightweight material such as fiberglass or plastic with a diameter that is less than the diameter of the outer sheath 102. For example, in one embodiment, the diameter of the introducer device 100 is in an inclusive range of 1 millimeter (mm) to 5 mm, such as 2 millimeters (mm) and may be equal to the diameter of the tissue examination probe. The length of the introducer device 100 is greater than the length of the outer sheath 102 and may be approximately 10 cm, 15 cm, 30 cm, 50 cm or greater in length.

According to some implementations, the length of the introducer device 100 is based on the type of tissue examination procedure being performed and how far the outer sheath 102 is inserted into a bodily orifice or surgical incision during the tissue examination procedure. For example, the length of introducer device 100 selected for a gastric endoscopy procedure where the introducer device 100 is inserted through a patient's mouth and into the stomach may be longer than the introducer device 100 selected for a neurological tissue examination procedure where a neurosurgeon inserts the introducer device 100 into a surgical incision to guide the outer sheath 102 to a cranial tissue site. In addition, at least one end of the introducer device 100 is tapered into a cone-like shape to allow for ease of insertion and removal of introducer device 100 into and out of the outer sheath 102.

FIG. 1B is an exemplary illustration of the outer sheath 102, according to certain embodiments. The outer sheath 102 is a hollow, tube-like structure into which the introducer device 100 is inserted to guide the outer sheath 102 to a desired location for the tissue examination procedure. Once the outer sheath 102 is in place and the introducer device 100 is removed from the outer sheath 102, a tissue examination probe is inserted into the outer sheath 102 and is guided to a tissue examination site by a medical professional. In certain implementations, the outer sheath 102 is made of a hard, flexible material such as rubber, TEFLON, or the like. The outer sheath 200 has a diameter that is greater than the diameters of the introducer device 100 and the tissue examination probe such that the introducer device 100 and the tissue examination probe are smoothly inserted and removed from the outer sheath 200. For example, in one embodiment, the diameter of the outer sheath 102 is in an inclusive range of 2 mm to 6 mm, such as 3 mm. The length of the outer sheath 102 is less than the length of the introducer device 100 and may be approximately 8 cm, 10 cm, 15 cm, 30 cm, or greater in length.

The outer sheath 102 includes one or more wings 104 to affix the outer sheath 102 at a predetermined location based on the type of tissue examination procedure being performed. The wings 104 are tab-like sections extending from the outer sheath 102 that can be peeled away from the surface of the outer sheath 102 along one or more longitudinal axes. The wings 104 produce surfaces that can be attached to one or more locations of a patient's body via sutures, clips, tape, or the like, so that the outer sheath 102 remains in a stationary position during the tissue examination procedure.

FIG. 1C is an exemplary illustration of the outer sheath 102 surrounding an introducer device 100, according to certain embodiments. The introducer device 100 has a greater length than the outer sheath 200 so that introducer device 100 can be more easily inserted into and removed from the outer sheath 102. The tapered end of the introducer device 100 is inserted to the bodily orifice or surgical incision of the patient's body to gain access to the tissue examination site. When the introducer device 100 and outer sheath 200 are at the desired location, the one or more wings 104 are pulled away from the surface of the outer sheath 102 to produce a surface for affixing the outer sheath 102 to the one or more locations of a patient's body via sutures, clips, tape, or the like, so that the outer sheath 102 remains in a stationary position during the tissue examination procedure.

FIG. 2A is an exemplary illustration of a tissue examination probe 200, according to certain embodiments. The tissue examination probe 200 is an elongated member that is cylindrical in shape and includes a first scanner 202 attached to a distal tip of the tissue examination probe 200 and a second scanner 204 surrounding a surface of the tissue examination probe 200 adjacent to the first scanner 202. The tissue examination probe 200 is made of soft, pliable material, such as plastic, rubber, flexible metal, and the like. In addition, the tissue examination probe 200 is made of a material that is non-magnetic so that the tissue examination probe 200 can be used in conjunction with other types of medical imaging procedures, such as magnetic resonance imaging (MRI), X-rays, computed tomography (CT) scans, and the like.

In some implementations, the shape of the tissue examination probe 200 has a main shaft that is circular, elliptical, square, rectangular, diamond, or any other shape that allows the tissue examination probe 200 to enter a surgical incision of a body and come in contact with tissues that are under examination. According to certain embodiments, the tissue examination probe 200 can be stiffened and/or strengthened based on the type of tissue examination procedure being performed as well as the system of the body being examined. For example, the main shaft of the tissue examination probe 200 can be stiffened via an external sheath that wraps around a circumference of the tissue examination probe 200. An internal stent or an internal air bladder can also be embedded into the tissue examination probe 200 in order to provide a greater amount of stiffness.

In addition, the first scanner 202 and the second scanner 204 can be any shape that accommodates the shape of the tissue examination probe 200. In some implementations, more than two scanners are included on the tissue examination probe 200. According to certain embodiments, the first scanner 202 has a wide angle scanning lens with a diameter in an inclusive range of 1 millimeter (mm) to 5 mm, such as 2 millimeters (mm). The second scanner 104 has a length in an inclusive range of 5 mm to 30 mm, such as 10 mm, that wraps around an outer surface of the tissue examination probe 200. The length of the tissue examination probe 200 is in an inclusive range of 50 centimeters (cm) to 150 cm, and in one implementation is 100 cm. The diameter of the tissue examination probe 200 is in an inclusive range of 1 mm to 5 mm, such as 2 mm.

In some implementations, the first scanner 202 and second scanner 204 include one or more microscopic optical and/or digital sensors that obtain images of the tissue being examined. For a given location of the tissue examination probe 2000, the first scanner 202 and the second scanner 204 are able to obtain images covering approximately a 360-degree field of view. In addition, the one or more sensors can include charged-coupled device (CCD) cameras, complementary metal-oxide semiconductor (CMOS) cameras, and other types of digital cameras.

The first scanner 202 and the second scanner 204 operate using one or more levels of digital and/or optical magnification. In some implementations, the first scanner 202 and the second scanner 204 are included in a telescopic rod lens system that includes one or more lenses for obtaining microscopic images, one or more digital cameras, and fiber optic cables that provide image illumination. In addition, the first scanner 202 and the second scanner 204 of the tissue examination probe 200 may include one or more bundles of flexible glass fibers to transmit tissue images. In certain embodiments, the magnification level of the first scanner 202 and the second scanner 204 is modified based on digital magnification performed by the one or more digital cameras within the tissue examination probe 200. For example, the second scanner 204 achieves one or more levels of magnification that include 10×10, 20×10, 40×10, and 100×10 magnifications of the field of view, according to certain embodiments. In one implementation, the one or more digital cameras of the first scanner 202 and second scanner 204 capture the tissue images at one magnification level, and the image magnification is performed by image processing circuitry of the backend system, which will be discussed further herein.

While the description above describes the first scanner 202 and second scanner 204 including fiber optic cables that emit visible light for illumination of the area being examined, the present disclosure also includes other illumination sources. For example, one or more metal halide, mercury, xenon and LEDs may be used to emit light to the illuminate the examination area. The first and second scanners (202 and 204) may include sensors that detect light in the visible spectrum, however these sensors may also include illumination source/filter pairs that detect other types of energy that is not in the visible band, such as infrared source/detector pairs, and ultraviolet source/filter pairs. Furthermore, filter sets may be included in the detectors to match spectral profiles of the light sources in order to isolate selected wavelength bands within a 300 nm to 700 nm range for example. The first and second scanners (202 and 204) may also include light sources that provide gentle LED illumination to support inspection of fluorescence signals from the tissue using fluorescence microscopy. Moreover, the tissue under examination may be stained with fluorescent stains (e.g., 4',6-diamidino-2-phenylindole) or, in the case of biological samples, expression of a fluorescent protein (e.g., green fluorescent protein). Alternatively the intrinsic fluorescence of a sample (i.e., autofluorescence) can be used. This approach allows for examination of the distribution of proteins or other molecules of interest.

The tissue examination probe 200 includes circuitry that provides intraoperative orientation to the surgeon as the tissue examination probe 200 is manipulated within the body. In one implementation where the tissue examination probe 200 is used in neurosurgery, neuro-navigation circuitry in the tissue examination probe 200 communicates with a neuro-navigation system that includes one or more cameras, reference points, monitors, and circuitry that directs the surgeon navigating the probe to a cerebral tissue location via a wireless or wired connection. The tissue examination probe 200 can also include a solid state compass, accelerometer, and other sensors that detect movement of the probe and can be included in determining the location of the tissue examination probe 200 within the body.

In certain embodiments, the first scanner 202 and the second scanner 204 are electrically connected to each other by flexible, optical fiber. In addition, the first scanner 202 and second scanner 204 are electrically connected to the backend system via a cord 210. The cord 210 includes an outer surface that houses at least one optical fiber that transmits the images obtained by the first scanner 202 and the second scanner 204. The outer surface of the cord 210 is made of a flexible material such as plastic, flexible metal, and the like. In certain embodiments, the outer surface is made of a material that is non-magnetic so that the tissue examination probe 200 can be used in conjunction with other imaging equipment, such as MRI. In some implementations, the tissue examination probe 200 includes circuitry to allow the tissue examination probe 200 to wirelessly communicate with the backend system, and the cord 210 may not be included.

A grasping mesh 206 is connected to a distal end of the tissue examination probe 200 and surrounds the first scanner 202 and the second scanner 204. The grasping mesh is a net-like structure that expands to surround a section of tissue to be examined and contracts to pull the tissue toward the first scanner 202 and second scanner 204. In the illustration of FIG. 2A, the grasping mesh 206 is in a contracted position where the grasping mesh 206 is pulled toward the first scanner 202 and second scanner 204. In some implementations, the grasping mesh 206 is made of interleaved carbon fibers, titanium, fiberglass, or another soft material that would minimize an amount of damage to the tissue being examined as the tissue is grabbed by the grasping mesh 206. The length of the grasping mesh 206 is in an inclusive range from 10 mm to 50 mm, such as 25 mm. According to one implementation, the grasping mesh 206 extends past a distal tip of the tissue examination probe 200.

The grasping mesh 206 expands and contracts based on operation of a grasping mesh operator 210 located at a proximal end of the tissue examination probe 200 at a location that may be convenient for a medical professional who is performing tissue examination procedures to operate. For example, the grasping mesh operator 210 may be in an inclusive range of 10 mm to 30 mm from the proximal end of the tissue examination probe 200, such as 20 mm, according to certain embodiments.

The grasping mesh operator 210 can include one or more buttons, knobs, or other devices that have corresponding circuitry to issue control signals via fiber optic cables connecting the grasping mesh operator 210 to the grasping mesh 206 to expand or contract the grasping mesh 206 based on how the grasping mesh operator 210 is manipulated. For example, if the grasping mesh operator 210 is a knob, then turning the knob in a clockwise direction may cause the grasping mesh 206 to expand to surround a section of tissue being examined. When the grasping mesh operator 210 is turned in a counter-clockwise direction, the grasping mesh 206 contracts to pull the tissue toward the first scanner 202 and the second scanner 204.

In some implementations, the grasping mesh 206 is embedded with optical fibers that illuminate an area surrounding the distal end of the tissue examination probe 200. As the tissue examination probe 200 is navigated to the tissue examination site with the grasping mesh 206 in the contracted position, the illuminated fibers assist the medical professional navigating the tissue examination probe 200 to the desired tissue site. For example, the first scanner 202 and second scanner 204 are used to visualize the path for the tissue examination probe 200, and the illuminated fibers of the grasping mesh 206 illuminate the images obtained by the first scanner 202 and second scanner 204.

The tissue examination probe 200 also includes a suction controller 212 that applies a predetermined amount of suction to the grasping mesh 206 when the grasping mesh 206 is surrounding a section of tissue to be examined. For example, when suction is applied via the suction controller 212 to the grasping mesh 206 surrounding a section of tissue, the tissue is further drawn toward the first scanner 202 and second scanner 204. The suction controller 212 can also apply suction pressure to reduce the amount of fluid surrounding the tissue so that the images obtained by the first scanner 202 and second scanner 204 more clearly show the tissue under examination.

FIG. 2B is an exemplary illustration of an expanded grasping mesh 206 on the tissue examination probe 200, according to certain embodiments. During the tissue examination procedure, the grasping mesh 206 is expanded via operation of the grasping mesh operator 210 to surround a section of the tissue being examined. When the grasping mesh 206 is subsequently contracted to pull the tissue toward the first scanner 202 and second scanner 204, the illuminated fibers in the grasping mesh 206 provide a back light source that illuminates the tissue from an opposite side of the tissue site from the first scanner 202 and second scanner 204. The light rays from the back light of the illuminated fibers pass through the tissue that has been grasped by the grasping mesh 206, which may allow the images obtained by the first scanner 202 and second scanner 204 to more clearly show features of the tissue that are used to identify the type of tissue during the tissue identification process, as will be discussed further herein.

Figure 3:
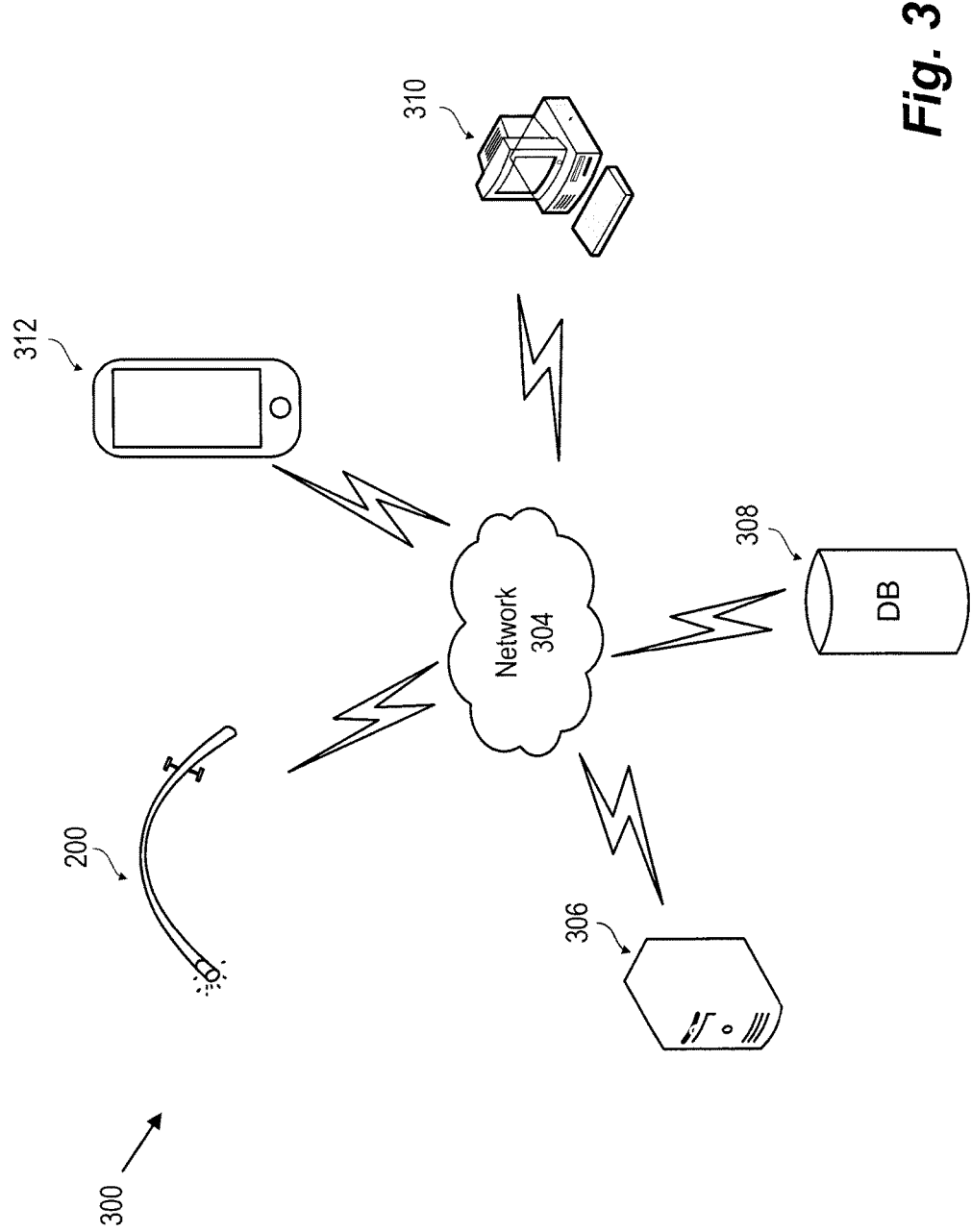
FIG. 3 is an exemplary illustration of a histopathology system, according to certain embodiments.

FIG. 3 is an exemplary illustration of a histopathology system 300, according to certain embodiments. The tissue examination probe 200 is connected to a backend system, which includes a server 306, database 308, computer 310, and mobile device 312 via a network 304. In some embodiments, more than one tissue examination probe 200 is included in the histopathology system 300. As such, the terms referring to the one or more than one tissue examination probe 200 can be used interchangeably. The tissue examination probe 200 can have a wired or wireless connection with the backend system.

The server 306 represents one or more servers connected to the computer 310, the database 308, the mobile device 312, and the tissue examination probe 200 via the network 304. The server 306 includes processing circuitry that executes one or more software processes related to capturing tissue images via the tissue examination probe 200, performing digital staining procedures, and matching the tissue images obtained by the tissue examination probe 200 to the tissue samples of the histopathological library stored in the database 308. The processing circuitry of the server 306 also executes one or more software processes related to implementing augmented reality features to a tissue examination procedure. Details regarding the software processes performed by the processing circuitry of the server 306 will be discussed further herein.

The computer 310 acts as a client device that is connected to the server 304, the database 308, the mobile device 312, and the tissue examination probe 200 via the network 304. In some implementations, the computer 310 is located in the operating room where the medical professional performing the tissue examination procedure can view the monitor of the computer 310 as the tissue examination probe 200 acquires the tissue images and provide inputs and amplifying information via an interface. In certain embodiments, the computer 310 is in a pathology lab outside the operating room where the tissue examination procedure is performed, and pathologists view the images on the computer 310 and provide feedback regarding tissue images obtained by the tissue examination probe 200.

The database 308 represents one or more databases connected to the computer 310, the server 306, the mobile device 312, and the tissue examination probe 200 via the network 304. In some implementations, a histopathological library is stored in the database 308 that includes a plurality of types of healthy and diseased tissue samples that are compared to the tissue being examined. For example, when the tissue images obtained by the first scanner 202 and second scanner 204 are transmitted to the backend system, the processing circuitry of the server 306 performs a matching algorithm to determine if the tissue being examined matches any of the tissue samples in the histopathological library. Details regarding the matching algorithm are discussed further herein.

The mobile device 312 represents one or more mobile devices connected to the computer 310, the server 306, the database 308, and the tissue examination probe 200 via the network 304. The network 304 represents one or more networks, such as the Internet, connecting the computer 310, the server 306, the database 308, the mobile device 312, and the tissue examination probe 200. The network 304 can also represent any other type of wireless network such as WI-FI, BLUETOOTH, cellular networks including EDGE, 3G and 4G wireless cellular systems, or any other wireless form of communication that is known.

As would be understood by one of ordinary skill in the art, based on the teachings herein, the mobile device 312 or any other external device could also be used in the same manner as the computer 310 to view the tissue images obtained by the tissue examination probe 200 as well as the matched tissues from the histopathological library. For example, as the surgeon advances the tissue examination probe 200 through the outer sheath 102 and into the tissue being examined and obtains images of the tissue via the first scanner 202 and the second scanner 204, a pathologist in the operating room or in a laboratory views the images obtained by the tissue examination probe 200 and one or more matched tissue images at an interface at the computer 310 or via an application on the mobile device 312. The pathologist can then select one or more of the matched tissue images as a most likely candidate for the type of tissue being examined and can add annotations to the images obtained by the tissue examination probe 200.

The information input by the pathologist at the computer 310 or mobile device 312 is received by the server 306. The server 306 transmits the information input by the pathologist to the computer 310 and/or mobile device 312 of the surgeon in the operating room. The information input by the pathologist and/or surgeon is also stored in the database 308 and can be accessed during post-operative assessments as well as future surgeries. Details regarding the processes performed by the histopathology system 300 are discussed further herein.

In some implementations, the histopathology system 300 performs augmented reality processes in which the surgeon documents details of the surgery via notes, images, video, and the like. The details of the surgery are associated with the location of the tissue examination probe 200 within the body and are stored in the backend system so that the details of the surgery can be accessed by the surgeon in future surgeries. For example, if the processing circuitry of the server 306 matches the tissue images obtained by the probe to cancerous tumor samples in the histopathological library, the surgeon can record amplifying information, such as the size of the tumor, characteristics of the cancerous cells, characteristics of the healthy cerebral cells, and location of the cancerous cells within the brain. During future surgeries, as the tissue examination probe 200 approaches the locations of where notes have been documented, the histopathology system provides the surgeon with the amplifying information that has been saved so that the surgeon can determine change in size of the cancerous tumor, effectiveness of treatments, and the like. Details of the documentation of amplifying information are discussed further herein.

Figure 4:
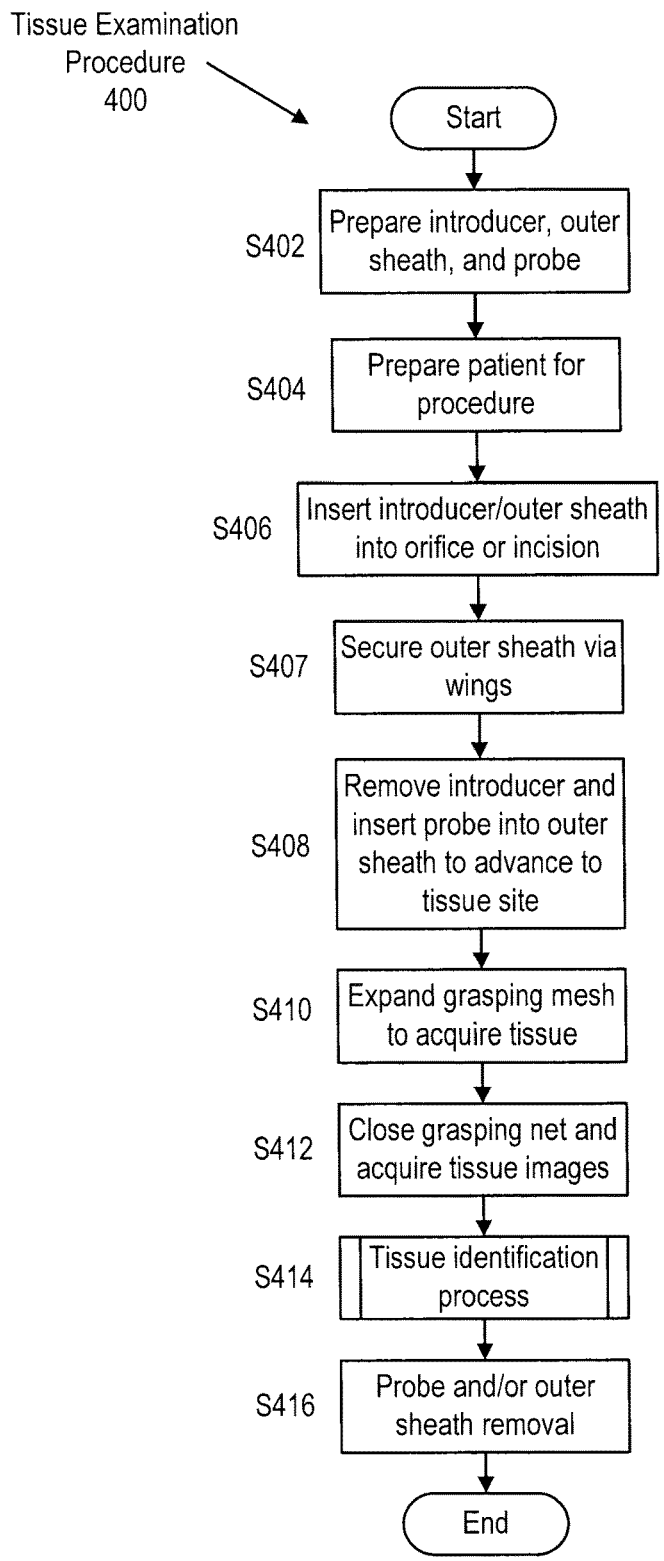
FIG. 4 is an exemplary flowchart of a tissue examination procedure, according to certain embodiments.

FIG. 4 is an exemplary flowchart of a tissue examination procedure 400, according to certain embodiments. At step S402, the introducer device 100, outer sheath 102, and tissue examination probe 200 are prepared for the tissue examination procedure 400. The medical professional selects the tissue examination probe 200 that will be used based on the amount of magnification by the first scanner 202 and the second scanner 204. For example, a tissue examination probe 200 with a largest amount of magnification may be selected to examine some types of neurons that are smaller and more densely populated than other types of neurons.

In addition, the tissue examination probe 200 can be stiffened and/or strengthened based on the type of tissue examination procedure being performed as well as the system of the body being examined. For example, the main shaft of the tissue examination probe 200 can be stiffened via an external sheath that wraps around a circumference of the tissue examination probe 200. An internal stent or an internal air bladder can also be embedded into the tissue examination probe 200 in order to provide a greater amount of stiffness.

According to some implementations, the lengths of the introducer device 100 and outer sheath 102 that are selected are based on the type of tissue examination procedure being performed and how far the outer sheath 102 is inserted into a bodily orifice or surgical incision during the tissue examination procedure. For example, the lengths of introducer device 100 and outer sheath 102 selected for a gastric endoscopy procedure where the introducer device 100 and outer sheath 102 are inserted through a patient's mouth and into the stomach may be longer than the introducer device 100 and outer sheath 102 selected for a neurological tissue examination procedure where a neurosurgeon inserts the introducer device 100 into a surgical incision to guide the outer sheath 102 to a cranial tissue site.

In addition, at least one end of the introducer device 100 is tapered into a cone-like shape to allow for ease of insertion and removal of introducer device 100 into and out of the outer sheath 102. The introducer device 100 has a greater length than the outer sheath 200 so that introducer device 100 can be more easily inserted into and removed from the outer sheath 102.

At step S404, the patient is prepared for the tissue examination procedure. In one implementation, the medical professional, such as the surgeon, gains access to the site of the tissue being examined by the tissue examination probe 200. For example, during surgery to locate and/or remove a brain tumor, the surgeon gains access to the cerebral tissue by making at least one surgical incision. In some implementations, the medical professional gains access to the tissue site through a natural orifice of the patient's body. For example, if tissue of the digestive system is being examined, the tissue examination probe 200 is advanced through the patient's mouth or anus depending on the section of the digestive system being examined.

At step S406, the introducer device 100 and surrounding outer sheath 102 are inserted into the bodily orifice or surgical incision into the patient's body. The tapered end of the introducer device 100 is inserted to the bodily orifice or surgical incision to gain access to the tissue examination site. The distance the introducer device 100 and outer sheath 102 are inserted is based on the distance from the tissue examination site to the bodily orifice or surgical incision where the introducer device 100 and outer sheath 102 are inserted and the system of the body being examined.

At step S407, the outer sheath 102 is secured via the one or more wings 104 on the outer sheath 102. When the introducer device 100 and outer sheath 200 are at the desired location, the one or more wings 104 are pulled away from the surface of the outer sheath 102 to produce a surface for affixing the outer sheath 102 to the one or more locations of a patient's body via sutures, clips, tape, or the like, so that the outer sheath 102 remains in a stationary position during the tissue examination procedure 400.

At step S408, the introducer device 100 is removed from the outer sheath 102 and the tissue examination probe 200 is inserted into the outer sheath 102 to be advanced to the tissue examination site. The medical professional inserts the tissue examination probe 200 into the outer sheath 102 and guides the distal tip of the tissue examination probe 200 to the location of the tissue being examined based on images obtained by the first scanner 202 and second scanner 204 as well as position-determining circuitry in the tissue examination probe 200.

In some implementations, the grasping mesh 206 is embedded with optical fibers that illuminate an area surrounding the distal end of the tissue examination probe 200. As the tissue examination probe 200 is navigated to the tissue examination site with the grasping mesh 206 in the contracted position, the illuminated fibers assist the medical professional navigating the tissue examination probe 200 to the desired tissue site. For example, the first scanner 202 and second scanner 204 are used to visualize the path for the tissue examination probe 200, and the illuminated fibers of the grasping mesh 206 illuminate the images obtained by the first scanner 202 and second scanner 204.

In some implementations, the processing circuitry of the server 306 is configured to implement augmented reality processes that save notes dictated and/or recorded by the medical professional and images obtained by the tissue examination probe 200 along with a corresponding location of the tissue examination probe 200 during the tissue examination. The notes and/or images are saved in the database 408 and accessed during future tissue examination procedures. For example, based on the location of the tissue examination probe 200 determined by the circuitry in the tissue examination probe 200 that provides intraoperative orientation, the processing circuitry of the server 306 outputs the notes and/or images that correspond to the locations of the tissue examination probe 200 from previous tissue examination procedures for the patient.

At step S410, the grasping mesh 206 is expanded to surround a section of the tissue being examined. In one implementation, the grasping mesh operator 210 is a knob on the tissue examination probe 200 that is turned in the clockwise direction to expand the grasping mesh 206 away from the tissue examination probe 200. The medical professional manipulating the tissue examination probe 200 can use images obtained by the first scanner 202 and second scanner 204 to ensure that the grasping mesh 206 is surrounding the tissue being examined.

At step S412, the grasping mesh 206 is closed around the section of tissue being examined, and the tissue is pulled toward the first scanner 202 and second scanner 204. In the example where the grasping mesh operator 210 is a knob, the grasping mesh operator 210 is turned in the counterclockwise direction to close the grasping mesh 206 around the tissue being examined. When the grasping mesh 206 contracts to pull the tissue toward the first scanner 202 and second scanner 204, the illuminated fibers in the grasping mesh 206 provide a back light source that illuminates the tissue from an opposite side of the tissue site from the first scanner 202 and second scanner 204. The light rays from the back light of the illuminated fibers pass through the tissue that has been grasped by the grasping mesh 206, which may allow the images obtained by the first scanner 202 and second scanner 204 to more clearly show features of the tissue that are used to identify the type of tissue during the tissue identification process of step S414.

The tissue examination probe 200 also includes a suction controller 212 that applies a predetermined amount of suction to the grasping mesh 206 when the grasping mesh 206 is surrounding the tissue to be examined. For example, when suction is applied via the suction controller 212 to the grasping mesh 206 surrounding a section of tissue, the tissue is further drawn toward the first scanner 202 and second scanner 204 via the applied suction. The suction controller 212 can also apply suction pressure to reduce the amount of fluid surrounding the tissue so that the images obtained by the first scanner 202 and second scanner 204 more clearly show the tissue under examination.

At step S414, the processing circuitry of the server 306 performs a tissue identification process as will be discussed further herein. At step S416, the tissue examination probe 200 is removed from the tissue examination site by pulling the tissue examination probe 200 out of the outer sheath 102. The outer sheath 102 is removed from the tissue examination site by disconnecting the one or more wings 104 from the locations where the wings 104 were attached at step S407. Once the wings 104 are disconnected, the outer sheath 200 is pulled out of the bodily orifice or surgical incision.

Figure 5:
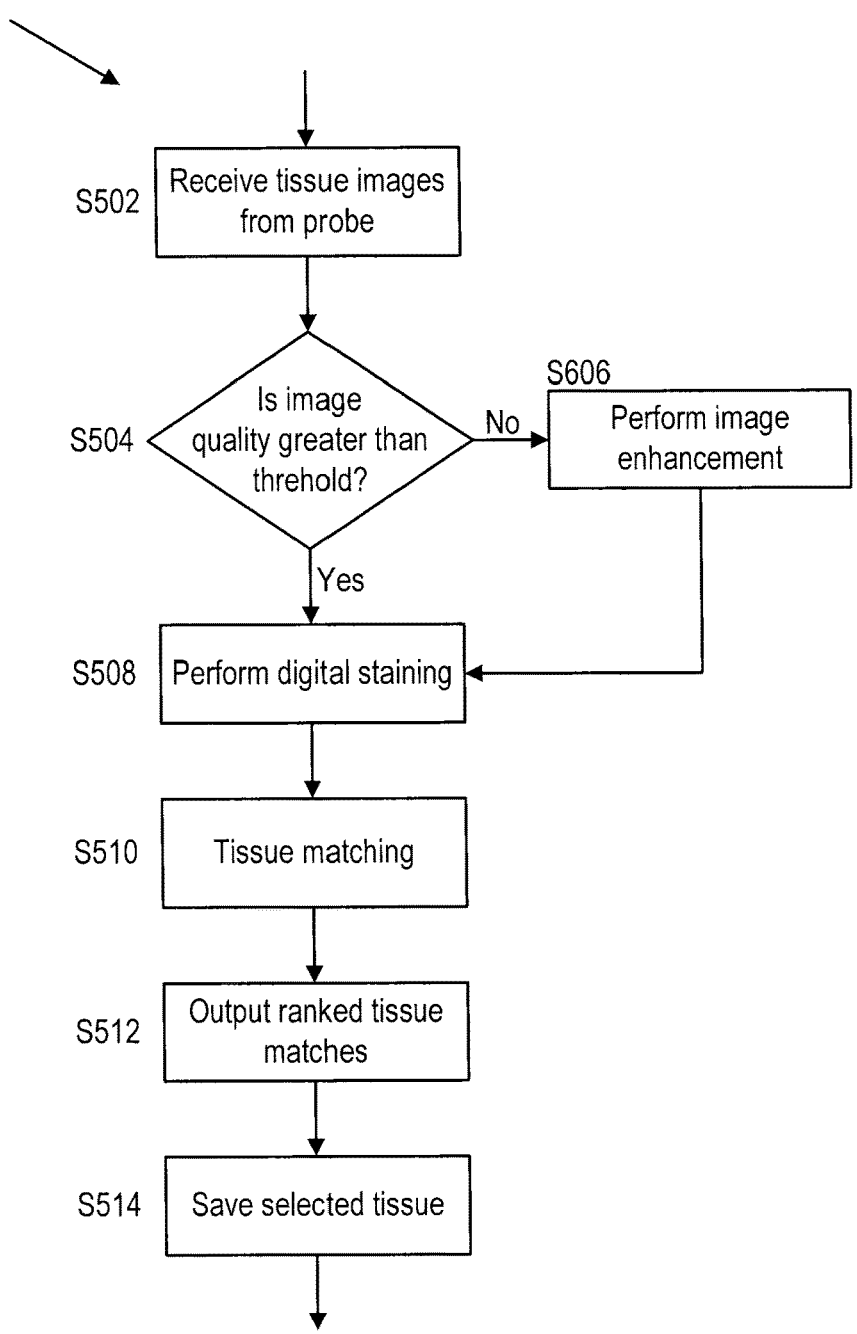
FIG. 5 is an exemplary flowchart of a tissue identification process, according to certain embodiments.

FIG. 5 is an exemplary flowchart for the tissue identification process of step S414, according to certain embodiments. At step S502, the processing circuitry of the server 306 receives the one or more tissue images obtained by the tissue examination probe 200 in the tissue examination procedure 400. The one or more unprocessed images are stored in database 308 and can be accessed in order to perform non-real time histopathology analysis. In some implementations, the processing circuitry of the server 306 performs digital magnification of the one or more tissue images obtained by the tissue examination probe 200.

At step S504, it is determined whether the quality of the images being processed is greater than a predetermined threshold. In certain embodiments, the images received from the tissue examination probe 200 are assigned a quality factor, such as a percentage of an approximate maximum image quality, based on overall clarity, detection of cell boundaries and cell components based on a shape of the cells being analyzed, and likelihood that the tissue will be correctly matched at step S510. In one implementation the predetermined threshold for the tissue image quality is set to 75% but can be modified to be any percentage based on examination conditions, type of tissue being examined, and the like. If the quality of the images obtained by the tissue examination probe 200 is greater than the predetermined threshold, resulting in a "yes" at step S504, then step S508 is performed. Otherwise, if the quality of the images obtained by the probe is less than the predetermined threshold, resulting in a "no" at step S504, then step S506 is performed.

At step S506, if it is determined at step S504, that the quality of the images obtained by the tissue examination probe 200 is less than the predetermined threshold, the images are enhanced to increase the quality. In some implementations, edge detection filters are applied to the images, and the contrast of the pixels of the boundaries of the cells and cell components is increased. If the quality of the images after the image enhancement is less than the predetermined threshold, then processing circuitry of the server 306 outputs an alert to the medical professional performing the tissue examination that the image quality is too low to accurately identify the tissue being examined. The alert is output via the computer 310 in the operating room or via the mobile device 312, so that the medical professional can acquire additional tissue images via the first scanner 202 and/or the second scanner 204.

At step S508, digital stains are applied to the tissue images obtained by the tissue examination probe 200. As used herein, the terms "stain" and "staining" can include without limitation staining with a dye or a stain, immunohistochemical staining, aptamer staining, tagging, chemical staining, antibody staining, or any other alteration to a tissue sample. Digital staining includes applying the one or more staining techniques to the tissue being examined with software processes that modify one or more pixels of the tissue images to highlight cell components, abnormalities, and the like. The processing circuitry of the server 406 determines the one or more digital stains to be applied to the tissue images based on the type tissue, type of diagnosis being performed, and the like. In some implementations, the medical professional manually inputs the one or more digital stains to be applied to the tissue images.

At step S510, a tissue matching algorithm is executed to match the tissue images obtained by the tissue examination probe 200 to one or more tissue samples in the histopathological library. In certain embodiments, the processing circuitry executes one or more matching and/or pattern recognition algorithms to determine that the tissue being examined shares one or more features with at least one tissue sample in the histopathological library. For example, when determining if brain tissue cells are cancerous, the processing circuitry of the server 306 compares the brain tissue cells obtained by the tissue examination probe 200 to cancerous and non-cancerous brain tissue samples stored on the histopathological library. If the brain tissue images share more common features with the cancerous tissue samples than the non-cancerous tissue samples, then the processing circuitry may determine that the brain tissue being examined by the tissue examination probe 200 may be cancerous. In some implementations, features of the tissue images are converted to feature vectors that are compared to feature vectors of the tissue samples in the histopathological library to determine one or more possible matches.

At step S512, the server 306 outputs a predetermined number of highest ranking matches determined at step S510. For example, the medical professional can indicate at the computer 310 for the server to output the top three tissue samples from the histopathological library that most closely match the tissue being examined by the tissue examination probe 200 based on the matching or pattern recognition algorithm implemented by the processing circuitry. In some implementations, the highest ranking matches are determined based on a number or percentage of common features shared between the tissue images obtained by the tissue examination probe 200 and the tissue samples of the histopathological library. In some aspects, the feature vectors of the tissue images obtained by the tissue examination probe 200 are compared to the feature vectors of the tissue samples in the histopathological library, and the server 306 outputs the types of tissue with a predetermined number of matching features. The medical professional, such as the surgeon or pathologist, then selects the most likely tissue sample candidate from the highest ranking matches output by the server 306.

If the processing circuitry is unable to match the tissue images obtained by the tissue examination probe 200 to the tissue samples of the histopathological library due to having approximately zero shared features between the tissue images and the tissue samples, the server 306 outputs an alert to the medical professional via the computer 310 or mobile device 312. In addition, if the processing circuitry outputs zero tissue matches, the medical professional can manually indicate for the processing circuitry to perform the digital staining of step S508 with a different digital staining technique and repeat the matching algorithm of step S510. The medical professional can also view the digitally stained images on the monitor of the computer 310 or the mobile device 312 and determine the type and characteristics of the tissue.

At step S514, the digitally stained tissue images are stored in the database 308 along with the amplifying information provided by the medical professional during the tissue examination procedure 400. FIG. 6 is an exemplary illustration of a matched tissue image with amplifying information, according to certain embodiments. In one implementation, the tissue examination probe 200 is used to obtain images of cerebral tissue to determine a location and size of a brain tumor. The one or more matched tissue images determined through the tissue identification process of step S414 include patient identification information, such as a name, identification number, date of procedure, name of surgeon, and type of procedure being performed. The matched tissue images also include the type of tissue identified along with notes and/or annotations made by the medical professional that may include size of tumor, location of the tumor, amount of magnification with scanner, type of digital stain used, and the like. The matched tissue images and the amplifying information is then stored in the database 308 with the patient's medical record and can be accessed during future tissue examination procedures to assess the success of treatments and monitor any changes in the tissue.

According to certain embodiments, the histopathology system 300 performs real time tissue identification, which allows medical professionals to provide immediate feedback regarding disease diagnoses and administer timely care to patients. By using the tissue examination probe 200 to locate and obtain images of the tissue and the processing circuitry of the server 306 to digitally stain and identify the tissue, identification of the tissue may not require obtaining an actual tissue sample that is analyzed in a laboratory. In addition, the medical professional, such as a surgeon, can take action to remove tissue that is identified as diseased without having to perform an additional surgery, which may cause additional stress to the patient and introduce complications. The histopathology system 300 can be implemented in medical disciplines where diagnosing cells as healthy or diseased in real time may improve an outcome for a patient, such as spinal and cerebral surgery, renal surgery, gynecological surgery, hepatic surgery, general surgery, and the like.

A hardware description of the server 306 according to exemplary embodiments is described with reference to FIG. 7. In some implementations, the hardware described by FIG. 7 also applies to the computer 310 or mobile device 312 to perform the processes as described previously herein. Implementation of the processes of the histopathology system 300 on the hardware described herein allows for increased speed and accuracy of pathology diagnoses. The server 306 includes a CPU 700 that perform the processes described herein. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the server 706 communicates, such as the computer 710.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

Figure 7:
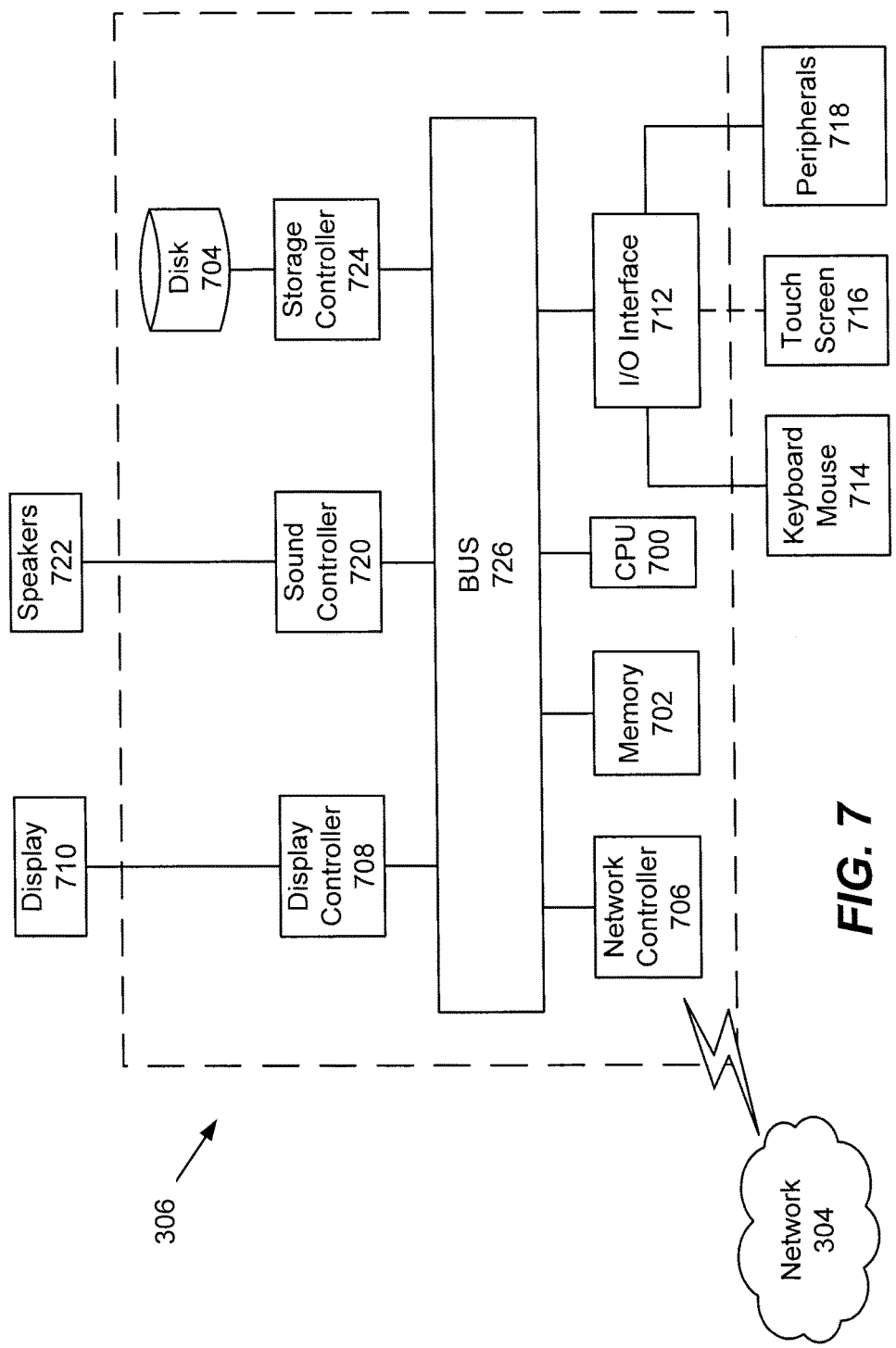
FIG. 7 illustrates a non-limiting example of a server for an emergency response system, according to certain embodiments.

The server 306 in FIG. 7 also includes a network controller 706, such as an Intel Ethernet PRO network interface card from Intel Corporation of America, for interfacing with network 304. As can be appreciated, the network 304 can be a public network, such as the Internet, or a private network such as an LAN or WAN network, or any combination thereof and can also include PSTN or ISDN sub-networks. The network 304 can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The server 306 further includes a display controller 708, such as a NVIDIA GeForce GTX or Quadro graphics adaptor from NVIDIA Corporation of America for interfacing with display 710 of the computer 310, such as a Hewlett Packard HPL2445w LCD monitor. A general purpose I/O interface 712 at the server 306 interfaces with a keyboard and/or mouse 714 as well as a touch screen panel 716 on or separate from display 710. General purpose I/O interface 712 also connects to a variety of peripherals 718 including printers and scanners, such as an OfficeJet or DeskJet from Hewlett Packard.

A sound controller 820 is also provided in the server 306, such as Sound Blaster X-Fi Titanium from Creative, to interface with speakers/microphone 722 thereby providing sounds and/or music. The general purpose storage controller 724 connects the storage medium disk 704 with communication bus 726, which may be an ISA, EISA, VESA, PCI, or similar, for interconnecting all of the components of the server 306. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

In other alternate embodiments, processing features according to the present disclosure may be implemented and commercialized as hardware, a software solution, or a combination thereof. Moreover, instructions corresponding to the tissue identification process of step S414 in accordance with the present disclosure could be stored in a thumb drive that hosts a secure process.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, an implementation may be performed on modules or hardware not identical to those described. Accordingly, other implementations are within the scope that may be claimed.

The invention claimed is:

1. A histopathology system comprising:
   an elongated, cylindrical probe having therein
      a first scanner connected to a distal tip of the probe,
      a second scanner surrounding a surface of the distal end of the probe adjacent to the first scanner, wherein the first and second scanner are configured to capture digital images of tissue,
      a mesh net connected to the distal end of the probe and configured to grasp tissue,
      a mesh net operator positioned at a proximal end of the probe, and
      control circuitry configured to
         expand and contract the mesh net to grasp the tissue in response to interaction with the mesh net operator, and
         indicate an intraoperative orientation of the probe as the probe is manipulated within a patient;
   a cylindrical outer sheath into which the probe is inserted having one or more tabs extending from the outer sheath to affix the outer sheath at one or more locations;
   an elongated, cylindrical introducer device configured to guide the outer sheath through a bodily orifice or surgical incision when the introducer device is inserted into the outer sheath; and
   at least one server with processing circuitry configured to
      receive tissue images from the probe, the tissue images being obtained by the first and second scanner,
      determine if image quality of the received tissue images is greater than a predetermined threshold,
      digitally stain the received tissue image when the image quality of the received tissue image is greater than the predetermined threshold,
      determine if one or more features of the stained tissue images match the at least one of the stored tissue samples,
      output a predetermined number of highest ranking matches, and
      store the stained tissue images in a database.

2. The system of Claim, 1 wherein the mesh net operator is positioned in an inclusive range from 10 mm to 30 mm from the proximal end of the probe.

3. The system of claim 2, wherein the mesh net operator is configured to issue control signals to expand or contract the mesh net.

4. The system of claim 3, wherein the control circuitry is configured to expand the mesh net operator when the mesh net operator is rotated in a clockwise direction and contract the mesh net is rotated in a counter-clockwise direction.

5. The system of claim 1, wherein the probe includes a suction connection to draw the tissue being examined toward the one or more scanners.

6. The system of claim 1 wherein the mesh net comprises at least one of interleaved carbon fibers, titanium, and fiberglass.

7. The system of claim 6, wherein a length of the mesh net is in an inclusive range from 10 mm to 50 mm.

8. The system of claim 6, wherein the mesh net includes embedded optical fibers to illuminate an area surrounding the distal end of the probe.

9. The system of claim 8, wherein the embedded optical fibers of the mesh net illuminate a path for navigation of the probe within a body.

10. The system of claim 8, wherein the embedded optical fibers provide a back light to illuminate the tissue being examined when the mesh net surrounds the tissue being examined.

11. The system of claim 1, wherein a length of the probe is in an inclusive range of 50 cm to 150 cm.

12. The system of claim 1, wherein a diameter of the probe is in an inclusive range of 1 mm to 5 mm.

13. The system of claim 1, wherein the outer sheath comprises at least one of TEFLON or rubber.

14. The system of claim 13, wherein the outer sheath has a diameter in an inclusive range of 2 mm to 6 mm and is greater than diameters of the probe and the introducer device.

15. The system of claim 13, wherein a length of the outer sheath is less than a length of the introducer device.

16. The system of claim 1, wherein the one or more tabs are configured to be pulled away from the outer sheath along a longitudinal axis.

17. The system of claim 16, wherein the one or more tabs are affixed at one or more bodily locations via at least one of sutures, clips, and tape.

18. The system of claim 1, wherein the introducer device has at least one tapered end to be inserted into the bodily orifice or surgical incision when inserted in to the outer sheath.

19. An apparatus for examining tissue comprising:
   an elongated, cylindrical probe having therein
      a first scanner connected to a distal tip of the probe,
      a second scanner surrounding a surface of the distal end of the probe adjacent to the first scanner, wherein the first and second scanner are configured to capture digital images of tissue,
      a mesh net connected to the distal end of the probe and configured to grasp tissue,
      a mesh net operator positioned at a proximal end of the probe, and
      control circuitry configured to
         expand and contract the mesh net to grasp the tissue in response to interaction with the mesh net operator, and
         indicate an intraoperative orientation of the probe as the probe is manipulated within a patient;
   a cylindrical outer sheath into which the probe is inserted having one or more tabs extending from the outer sheath to affix the outer sheath at one or more locations; and
   an elongated, cylindrical introducer device configured to guide the outer sheath through a bodily orifice or surgical incision when the introducer device is inserted into the outer sheath,
   wherein the tissue images obtained by the first and second scanner are transmitted to a server, wherein the server is configured to
      determine if image quality of the tissue images is greater than a predetermined threshold, digitally stain the tissue image when the image quality of the tissue image is greater than the predetermined threshold,
determine if one or more features of the stained tissue images match the at least one of stored tissue samples,
output a predetermined number of highest ranking matches, and
store the stained tissue images in a database.

* * * * *